United States Patent [19]

Wegener et al.

[11] Patent Number: 4,627,426

[45] Date of Patent: Dec. 9, 1986

[54] TEAR-AWAY STERILE AND ABSORBENT SHEET FOR OPERATING TABLE USE

[75] Inventors: Jack Wegener, Gloucester, N.J.; Raynor A. Johnson, Newark, Del.; Robert Weedling, Stockertown, Pa.

[73] Assignee: American Industrial Research, In., Newark, Del.

[21] Appl. No.: 735,233

[22] Filed: May 17, 1985

[51] Int. Cl.⁴ .............................................. A61F 13/00
[52] U.S. Cl. .................................. 128/132 R; 428/43; 5/487
[58] Field of Search ........................ 128/132 R, 132 D; 428/43; 5/487

[56] References Cited

U.S. PATENT DOCUMENTS

| | | | |
|---|---|---|---|
| 3,030,957 | 4/1962 | Melges | 128/132 D |
| 3,260,260 | 7/1966 | Questel | 128/132 D |
| 3,273,176 | 9/1966 | Millar | 5/487 X |
| 3,380,086 | 4/1968 | McCurry | 5/487 |
| 4,253,451 | 3/1981 | Solomon | 128/132 D |
| 4,358,865 | 11/1982 | Pagel et al. | 428/43 X |

FOREIGN PATENT DOCUMENTS 2399824  4/1979  France ............ 128/132 R

*Primary Examiner*—Nancy A. B. Swisher
*Attorney, Agent, or Firm*—Sughrue, Mion, Zinn, Macpeak & Seas

[57] ABSTRACT

A highly absorbent sheet or pad sized to and placed onto the top of an operating table is weakened longitudinally through the center to form paired separable center-joined sections for lateral removal to respective sides of a patient lying on the sheet and centered longitudinally therewith. After surgery, the absorbent pad carrying a significant mass of blood can be quickly removed from the patient by pulling with sufficient force on the opposites sides of the pad, severing the pad centrally at the weakened portion. The weight of the patient tends to maintain one section of the pad beneath that portion of the patient as the other section is torn laterally away from the one section. The pad may comprise several layers with one or more layers being weakened by thinning the sheet material or perforating the same longitudinally. Velcro material in strip form on the table and on the bottom of the pad may be employed for releasably fixing the pad on the table at a desired position but permitting removal of the pad after severing of the same along the longitudinal center line. Dual, opposite folded sheet sections linked by tabs at the center folds with the fold openings to the outside constitute an alternative pad or sheet for such use.

8 Claims, 8 Drawing Figures

TEAR-AWAY STERILE AND ABSORBENT SHEET FOR OPERATING TABLE USE

FIELD OF THE INVENTION

This invention relates to absorbent sheets or pads normally positioned on an operating table between the patient and the table for absorbing blood and other liquids released from the patient during the course of an operation, and more particularly, to a tear-away sterile absorbent sheet or pad which may be readily removed from the patient without any patient discomfort by severance of the pad sectionally to facilitate that removal.

BACKGROUND OF THE INVENTION

Conventionally, operating table tops are covered with a single layer cotton sheet whose edges drape down at the table sides. During the course of an operation, a significant amount of blood tends to escape from the patient and is absorbed by the cotton sheet. After the operation, it is difficult to remove the sheet from the table top due to the weight and mass of the patient overlying the same. Typically, the patient must be log-rolled, that is, rolled over towards one side of the table, the sheet folded over towards that side, the patient rolled to the opposite side and off the sheet and then the sheet is removed from the table top.

Log-rolling is often difficult due to the weight and mass of the patient. Secondly, the patient is in the worst possible condition to be moved, both because of the operation performed and additionally because, while under anesthesia, the body does not employ its normal defense mechanisms to forced movement. Thus, the patient may bruise portions of the body during logrolling or other forced movement necessary to remove the blood soaked operating table cloth or cover sheet.

Within recent years, the applicants have developed a patient mover for facilitating the movement of patients in hospitals to and from gurneys, hospital beds, operating tables, X-ray equipment such as particularly CAT scanners and the like as set forth in U.S. Pat. No. 4,272,856. The patient mover employs a plenum chamber formed by several thin flexible sheets, sealed together about their edges, subjected to low pressure air to inflate the plenum chamber to the extent of lifting the patient. The bottom thin flexible sheet bears thousands of pinhole type perforations through which air escapes to create a thin air film bearing between the bottom of the patient mover and the underlying relatively rigid support surface such as the operating table, gurney top, hospital bed, etc. Such patient movers, which are somewhat similar to an air mattress when inflated, lifts the patient up, with the low pressure air escaping through the holes creating a frictionless air bearing.

The patient mover thus facilitates the transfer of the patient to and from the operating table, and permits the patient to rest on the patient mover (whose air mattress or plenum chamber is deflated), a problem develops when an absorbent cotton sheet or chuck is placed over the patient mover for capturing the blood from the patient during an operation. After the operation, the cotton sheet must be removed prior to the patient being moved off the operating table while still on the same patient mover that placed him thereon prior to the operation.

It is, therefore, a primary object of the present invention to provide an improved, sterile, absorbent sheet or pad for use on an operating table during an operation for positioning between the patient and the operating table top which may be easily removed, which provides no trauma to the patient, and which absorbent sheet may be particularly useful as a sheet overlying an air bearing type patient mover.

SUMMARY OF THE INVENTION

The invention is directed to a tear-away sterile absorbent sheet or pad for operating table use and positioning between the patient and the operating table top. The absorbent material sheet comprises two center joined segments, weakened along the center thereof so as to separate down the middle for selective sidewise removal of the separated sections from respective sides of the patient by pulling the segments laterally to effect separation and removal without trauma to the patient lying thereon.

The sheet or pad may comprise multi-layer sheet material including an underlying liquid impervious layer extending the full width of the table and including a longitudinal weakened line through the center thereof. At least one upper absorbent layer may be fixed thereto as two separate segments in edge abutment in alignment with the weakened line within said bottom layer. The longitudinal weakened line may be a line of perforations within the bottom sheet. Alternatively, the weakened line may be a thinner portion of the impervious sheet material forming the bottom layer. The absorbent material sheet or pad may be a single, unitary absorbent material pad of single or multiple layer form, perforated down the longitudinal centerline throughout the pad layer or layers to define side-by-side separable center-joined segments. The absorbent material sheet or pad may further comprise a pair of edge-abutting folded absorbent sheet material sections with the folds being joined adjacent the sheet centerline with a weakened connection therebetween and opening laterally outwardly. The separate, folded sections of absorbent material sheet may be coupled together laterally at longitudinally spaced positions by tabs. Alternatively, the folded absorbent material sheet sections may be alternatively joined at the folds by a release adhesive.

The invention is further directed to the combination of an operating table and a tear-away sterile absorbent sheet or pad overlying the operating table top and removable therefrom. The sterile absorbent sheet or pad comprises an absorbent material pad consisting of two side-by-side, absorbent sheet material sections, Velcro strips fixed to the bottom of the segments facing the table top, and mating Velcro strips fixed to the table top sized to the Velcro strips borne by the pad segments and engagable therewith such that the pad segments may be torn away laterally from beneath a patient lying on the pad sections and aligned with the abutting edges of the sections, without trauma to the patient during removal thereof. Alternatively, clips borne by an operating table top or a patient mover thereon releasably hold the absorbent material pad sections in side-by-side position on the table top with the patient carried thereon, permitting the sections after unclipping to be separately removed from beneath the patient to respective sides thereof by pulling the sectionss laterally from beneath the patient and across the top of the operating table or patient mover.

DESCRIPTION OF THE PREFERRED EMBODIMENTS

Figure 1:
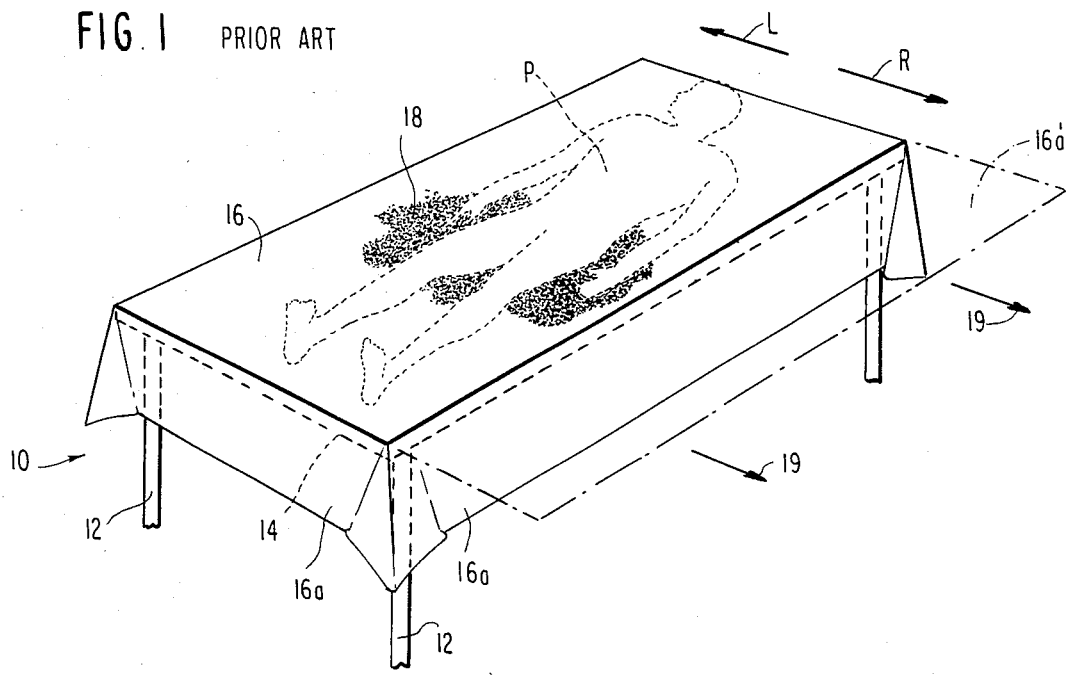
FIG. 1 is a perspective view of a conventional operating table bearing an absorbent cotton sheet for absorbing blood and other liquids seeping from a patient during an operation, with the patient overlying the absorbent cotton sheet and being centered thereon, constituting prior art practice.

Referring first to FIG. 1, the prior art, conventional operating room set up shown thereby involves an operating table, indicated generally at 10 including upright legs 12 bearing a horizontal operating table top at 14 upon which the patient P rests. Underlying the patient P is an absorbent cotton sheet or chuck 16 whose side edges 16a extend beyond the table top and down about the sides thereof. As discussed previously, typically during the operation, a large amount of liquid such as blood as at 18 may escape the patient and is thus absorbed by the underlying absorbent cotton sheet or chuck. In removal, the patient is log-rolled, first to the right as indicated by arrow R, whereupon, the portion of the cotton sheet 16 to the left is folded over such that when the patient P is then log-rolled to the left, as indicated by arrow L, he is moved off the sheet. This allows the sheet to be then removed, as indicated by paired arrows 19, by grasping side edge 16a and moving it in the direction of the dotted line as at 16a'. Conventionally, the patient is further log-rolled or lifted from the operating table to the top of a gurney (not shown) or equal height positioned to the side of the table and transported from the operating room.

Figure 2:
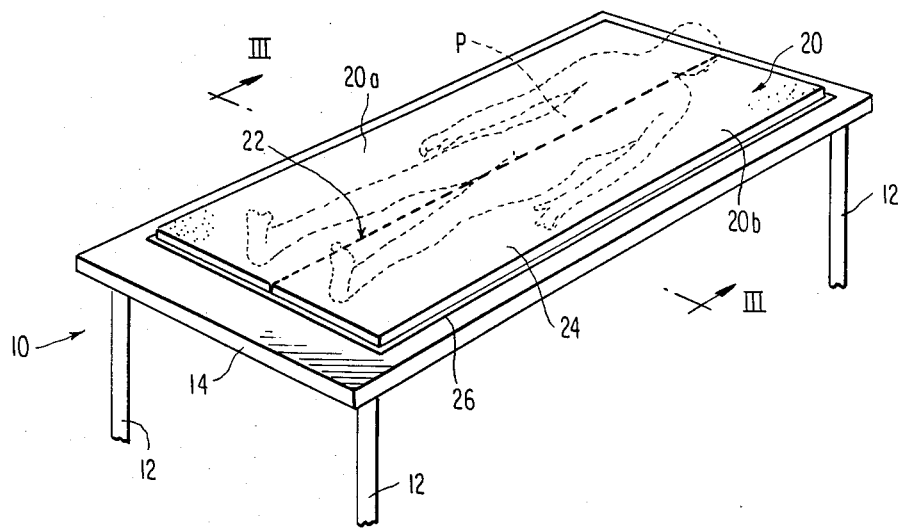
FIG. 2 is a perspective view of a tear-away sterile absorbent sheet forming a preferred embodiment of the present invention positioned on an operating table and beneath a patient, prior to severance into segments and removal from the patient in accordance with aspects of the present invention.
Figure 3:
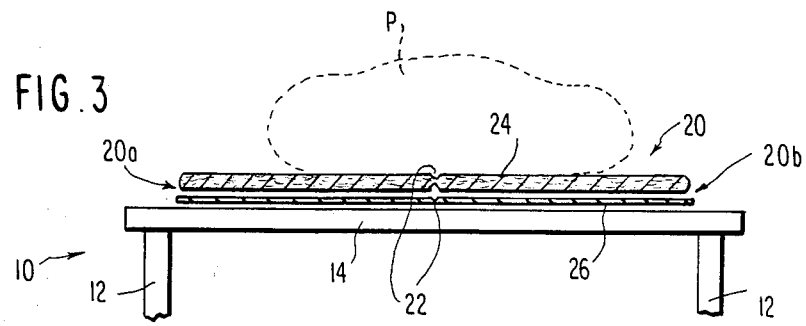
FIG. 3 is a vertical sectional view of the operating table set up as illustrated in FIG. 2, taken about line III—III.

Turning next to FIGS. 2 and 3, there is shown one embodiment of the present invention which eliminates trauma to the patient and prevents injury to the patient during the removal of an absorbent sheet, pad or chuck from the top of the operating table and beneath the patient. As may be seen, with respect to the embodiment of FIGS. 2 and 3 and the further embodiments of FIGS. 4-8 inclusive, like numerals have been employed for like elements. In that respect, the operating table 10 is the same as that shown in FIG. 1, and the patient is likewise designated at P. In this case, instead of an absorbent cotton sheet, there is provided one form of the tear-away sterile absorbent sheet or chuck, indicated generally at 20, lying underneath the patient P and aligned with the patient P.

As best seen in the vertical sectional view of FIG. 3, the absorbent sheet or chuck 20 is formed of at least two layers, an underlying inperforate flexible film sheet as at 26, and an overlying thick absorbent material pad 24. The absorbent chuck 20 may comprise multiple layers or a fairly thick non-woven absorbent material sheet capable of absorbing a significant amount of blood escaping from the patient P during the operation. In the embodiment of FIGS. 2 and 3, the center of the composite layer sterile absorbent sheet or chuck 20, along a longitudinal centerline, is weakened as at 22. This permits the sterile absorbent sheet 20 to be severed longitudinally at the weakened section by tearing away the right and left side segments or sections 20a, 20b of the absorbent sheet 20 from each other and from beneath the patient P to respective left and right sides thereof without discomfort or trauma to the patient. Severance occurs at the weakened line 22. In the embodiment of FIGS. 2 and 3, the weakened line is obtained by perforating both the upper absorbent sheet material pad 24 and the underlying impervious sheet 26, at 22.

Alternatively, a line of perforations may be provided within the overlying absorbent pad 24 while the underlying liquid impervious sheet 26 may be weakened by thinning that sheet along a narrow longitudinal centerline thereof. The bottom sheet 26 of this composite assembly may be formed of polyethylene, polyvinyl chloride or the like. The upper layer may be formed of a single or multi-ply absorbent paper of non-woven absorbent fiber or a composite of the same.

It should be appreciated that the left and right segments or sections 20a, 20b of the tear-away absorbent sterile sheet 20 may be removed from respective sides of the patient in sequence by pulling at one corner of the composite sheet 20, say from the head end of the patient towards the foot, thereby separating the two segments or sections progressively while at the same time sliding the torn segement out from beneath the patient diagonally to the centerline of the table, absorbent sheet, and patient P.

Figure 4:
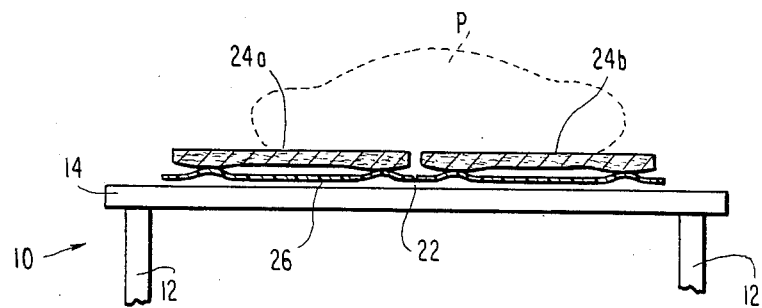
FIG. 4 is a vertical sectional view of an operating table set up forming a further embodiment of the present invention.

FIG. 4 is a vertical sectional view of a further embodiment of the invention, wherein a pair of side-by-side preseparated absorbent sheet material pads 24a, 24b are adhesively fixed or thermo-bonded to the upper surface of an underlying unitary thin flexible sheet 26. Sheet 26 bears a line of perforations 22 longitudinally through the center thereof which constitutes the weakened section of the sheet and permits sheet severance along that line in the manner of the embodiment of FIGS. 2 and 3.

In the alternative, instead of a line of perforations 22, a weakened line may be formed by thinning the thin flexible bottom sheet 26 longitudinally at its center.

Figure 5:
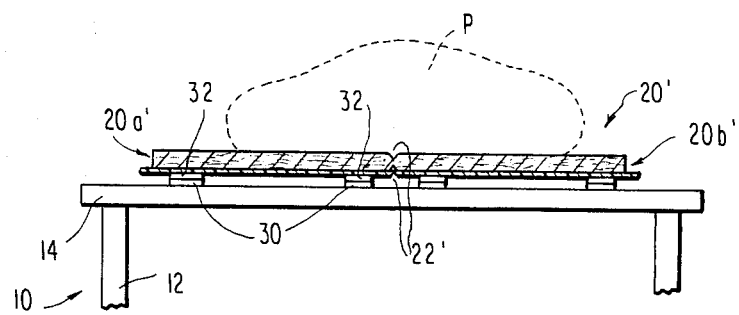
FIG. 5 is a vertical sectional view of yet another embodiment of the present invention.

FIG. 5 shows an alternative embodiment of the invention in which the patient P lies on a unitary absorbent pad 20' comprised of left side 20a' and right side 20b' which pad is separable at line of perforations as at 22' through the center of the same and longitudinally of the pad. In this arrangement, Velcro strips 30 are provided fixed to the table top 14 facing further engaging mating Velcro strips 32 borne by the pad segments 20a' and 20b'. This arrangement facilitates the maintenance of the pad segments or sections 20a' and 20b' in position prior to removal from beneath the patient and severance along the weakened line 22' joining the same. Alternatively, with respect to the embodiment of FIG. 5, the segments 20a' and 20b' may be preseparated pads which are simply placed in edge abutting position and held in place by the various Velcro strips 30, 32. As may be appreciated, the spacing provided by the Velcro pads is exaggerated simply to show the content of the Velcro strips as releasably holding the pad sections 20a' and 20b' in place on the table top 14 and maintained beneath the patient P prior to tearaway removal of the sections, side to side, in the same manner as the previously described embodiments of the invention.

Figure 6:
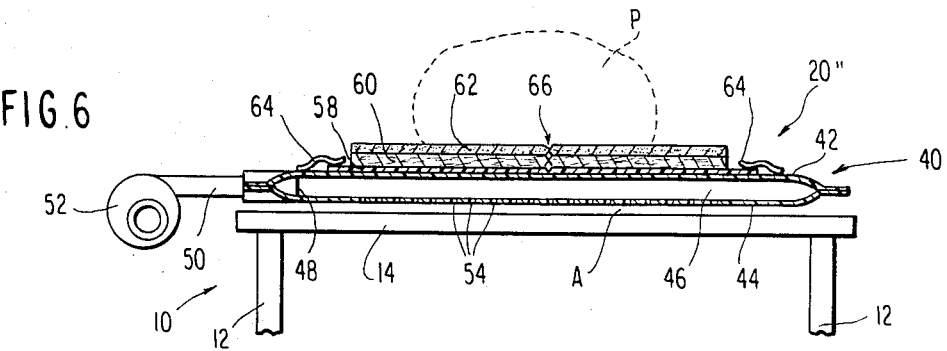
FIG. 6 is a vertical sectional view of a further embodiment of the present invention.

FIG. 6 illustrates a further embodiment of the invention as applied to an operating table 10 having positioned on table top 14 an air bearing type patient mover indicated generally at 40. The patient mover 40 may be similar to that found within our earlier U.S. Pat. No. 4,272,856, being, for example, of bag form including a top thin flexible sheet 42 overlying a bottom thin flexible sheet 44 and forming a plenum chamber 46 therebetween. The sheets may be formed of similar flexible film material such as polyvinyl chloride or polypropylene, of several mils thickness, and being of a material preferably permitting edge sealing of the sheets together about their peripheries by localized application of heat to thermo-bond the sheets together. Appropriately, in the schematic representation of FIG. 6, the plenum chamber 46 has an air inlet as at 48 through which projects, for instance, the end of a hose 50 from a battery powered blower 52 whose function is to feed low pressure air to plenum chamber 46. The plenum chamber 46 includes thousands of pinhole type perforations 54 within the thin flexible bottom sheet 44 underlying the load area, i. e. that of the patient P. Pressurization of the plenum chamber 46 results in jacking of the patient P off the top 14 of table 10 and the creation of an air bearing A between the table top 14 and the perforated portion of the thin flexible bottom sheet 44. The escape of air is at low CFM through the small diameter pinhole type perforations 54. In the manner of U.S. Pat. No. 4,272,856, a porous pad or chuck indicated generally at 20" is positioned overlying the top of the thin flexible imperforate sheet 42 of patient mover 40. The chuck 20", as may the other embodiments previously described, is formed by an underlying film 58 of a liquid impervious plastic, an intermediate thick porous absorbent material layer 60 and an upper porous gauze layer 62. The chuck or pad 20" may be mechanically coupled to the patient mover through a number of clips 64 fixed to the patient mover 40 and detachably coupled to the porous material chuck 20". In the embodiment of FIG. 6, the chuck 20" must be weakened longitudinally at its center, for instance, by providing a line of perforations as at 66 through all three layers 58, 60 and 62 of the chuck or pad 20". This permits the chuck or pad 20" to separate longitudinally down the centerline thereof for segmental removal of the two separated segments or sections, to the right and left of the patient P overlying the same and centered on the chuck. Such severance and removal occurs with the patient mover plenum chamber 46 deflated, in the manner of the prior embodiments. The patient P may then be transported from the operating table 20 in an easy and efficient manner after creation of the air bearing A in the manner of referred to U.S. Pat. No. 4,272,856.

Alternatively, the Velcro strips as at 30, 32 of FIG. 5, may be employed in lieu of clips 64 in the embodiment of FIG. 6 and in accordance with the teachings of U.S. Pat. No. 4,272,856. Further, the various layers 58, 60, and 62 of chuck 20" may be selectively weakened to permit tearing apart of all layers by means other than perforations as for instance by thinning the sheet material of a given layer such as the underlying imperforate sheet 58, along a longitudinal centerline. Also, it should be kept in mind that preferably the chucks, pads or sheets should have a bottom surface which is impervious to liquid so that blood or other liquid seeping from the patient during the operation is retained within the pad or absorbent material and does not leak onto the table top 14, via perforations.

Figure 7:
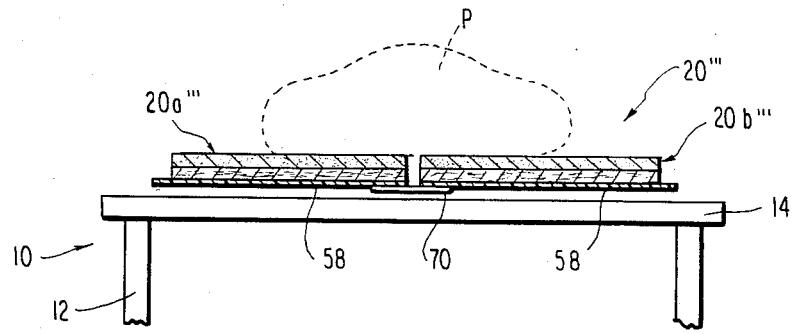
FIG. 7 is a vertical sectional view of a tear-away sterile absorbent sheet constituting another embodiment of the invention.

Turning to FIG. 7, a further embodiment of the invention utilizes a chuck or pad indicated generally at 20''' comprised of two separate pad portions as at 20a''', 20b''' joined by a number of lateral connecting tabs 70 which may be plastic strips easily tearable by maintaining the two pad sections 20a''' and 20b''' connected. The pad sections 20a''' and 20b''' may be made up in three layer form such as that of pad or chuck 20' in FIG. 6 and in accordance with the teachings of U.S. Pat. No. 4,272,856. Again, the patient P is centered on the chuck 20''' straddling the two chuck sections and the sections rest on the top 14 of the operating table 10. Removal is achieved in the same manner as the prior embodiments by pulling the sections 20a''', 20b''' to the left and right respectively, starting at one end, ripping the tabs or severing the tabs at their end connections to a pad section. The tabs may be thermo-bonded at their ends to the underlying imperforate sheet 58 of the chuck sections 20a''', 20b'''.

Figure 8:
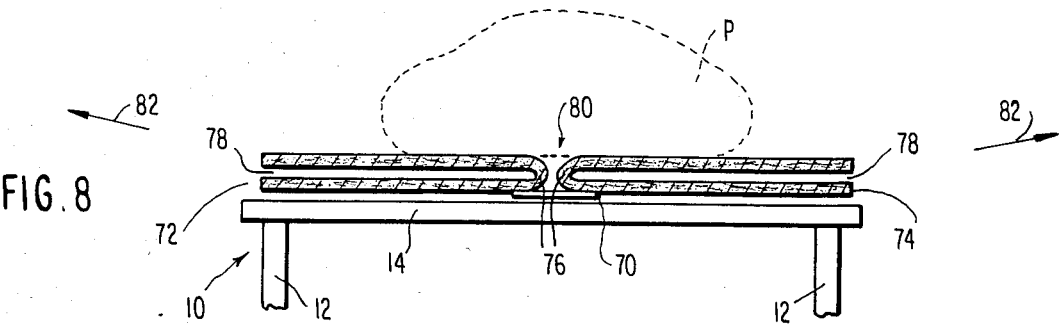
FIG. 8 is a vertical sectional view of an operating table set up showing yet a further embodiment of the tear-way sterile absorbent sheet of the present invention.

FIG. 8 is a modification of the arrangemnet employed in FIG. 7. In this case, however, a pair of separate porous sheets 72 and 74, having an overall width approximately equal to that of the operating table 10, are folded in half with their fold lines 76 in abutment or near abutment and having open ends 78 directed away from each other. The folded porous sheet sections 72, 74 may be joined together by a plurality of short length transverse tabs 70 which may be heat sealed at their ends to the respective sheet or pad sections 72, 74 at and spanning the gap between fold lines 76 of respective sheet sections 72, 74. The patient P overlies the joined sheet sections 72, 74, centered on gap 80, and supported by the operating table top 14 in the manner of the prior embodiments. Separation of the sections 72, 74 and removal from beneath the patient P without exerting trauma on the patient occurs by grasping a free edge such as the upper edge of right side sheet section 74 and pulling it outwardly from under patient P, while simultaneously or sequentially pulling the upper edge of the opposite sheet section 72 outwardly from under the patient P, all as indicated by arrows 82 in FIG. 8. The sheet sections 72, 74 may be formed of suitable porous pad material with the porous side thereof facing outwardly when folded in the manner shown in FIG. 8 so as to readily absorb the blood escaping the patient during the operation. Of course, fluids other than blood may be absorbed and retained within the sterile abosrbent sheet in pad, chuck or like form permitting ready disposal after removal under the separation techniques described in conjunction with the illustrated embodiments.

As may be appreciated, the tear-away sterile absorbent sheet of the present invention eliminates the log-rolling of the patient P which requires considerable effort and force and is particularly hazzardous to the health of a patient P immediately after an operation has been terminated and while under anesthesia with loss of muscle tone, bruising of the patient may result, due to sudden unanticipated movement without normal reflexes available to a patient who is asleep. Further, a pile of tear-away sterile absorbent sheets may be carried by the operating table, with the top sheet torn in two after the operation to expose a new top sheet fgor use in a succeeding operation involving a new patient.

While the invention has been particularly shown and described with reference to preferred embodiments thereof, it will be understood by those skilled in the art, that the foregoing and other changes in form and details may be made therein without departing from the spirit and scope of the invention.

What is claimed is:

1. A tear-way sterile absorbent material operating table sheet for operating table use, said absorbent material sheet being adapted for placement in an overlying position on the top of an operating table and between a patient centered longitudinally and laterally thereon and the table top, the improvement wherein said sheet is of a length on the order of the length of the patient and is of a width in excess of the width of the patient and comprises:

two separable sheet sections joined along a longitudinal centerline underlying and in line with the patient supported thereby by a weakened line extending longitudinally through the longitudinal centerline of said sheet, such that said sheet sections may be removed by tearing of the sheet along the weakened line from one end to the other by lateral pulling of the sections apart to effect separation and removal from beneath the patient, without moving the patient relative to the table top.

2. The sterile absorbent material operating table sheet as claimed in claim 1 wherein said sheet includes an underlying liquid impervious layer extending the full width of the sheet, said layer being longitudinally weakened along a centerline thereof, at least one overlying absorbent material layer as separate side-by-side segments of approximately one-half the width of the underlying layer.

3. The sterile abosrbent material operating table sheet as claimed in claim 2, wherein a line of perforations exits along the longitudinal weakened centerline of said underlying liquid impervious layer.

4. The sterile absorbent material operating table sheet as claimed in claim 3, wherein said underlying liquid impervious layer comprises a thin flexible plastic sheet, and a thinned portion of said thin flexible plastic sheet extends along said longitudinal centerline.

5. The sterile absorbent material operating table sheet as claimed in claim 4, comprising, in order, an underlying thin flexible film of a liquid impervious plastic, an intermediate relatively thick porous absorbent material layer, and an upper porous gauze layer, and wherein all three layers of said absorbent sheet are perforated down the longitudinal centerline of the sheet.

6. The sterile abosrbent material operating table sheet as claimed in claim 5, wherein said center joined separable segments comprise a pair of back-to-back folded absorbent sheet sections opening laterally away from each other, and weak connection means exist at said folds of said folded sheet sections such that separation at the center of said sheet may be effected by grasping a free end of each folded sheet material sections remote from the connection at said folds and pulling laterally to separate said sections and cause the one layer of each folded section to slide over the other layer thereof in being pulled laterally outwardly from beneath the patient.

7. The sterile absorbent material operating table sheet as claimed in claim 6, wherein said weak connection means is formed by a plurality of lateral tabs having opposite ends connected, respectively, to the folded sheet sections at the fold thereof.

8. The sterile absorbent material operating table sheet as claimed in claim 7, wherein said folded sections are joined at their folds, and wherein a line of perforations are formed within the joint between the folds.

* * * * *